United States Patent
Berger

(10) Patent No.: US 9,546,361 B2
(45) Date of Patent: Jan. 17, 2017

(54) THERMALLY STABLE ENZYMES, COMPOSITIONS THEREOF AND METHODS OF USING SAME

(71) Applicant: Lehigh University, Bethlehem, PA (US)

(72) Inventor: Bryan William Berger, Doylestown, PA (US)

(73) Assignee: Lehigh University, Bethlehem, PA (US)

( * ) Notice: Subject to any disclaimer, the term of this patent is extended or adjusted under 35 U.S.C. 154(b) by 0 days.

(21) Appl. No.: 14/435,037

(22) PCT Filed: Oct. 11, 2013

(86) PCT No.: PCT/US2013/064604
§ 371 (c)(1),
(2) Date: Apr. 10, 2015

(87) PCT Pub. No.: WO2014/059313
PCT Pub. Date: Apr. 17, 2014

(65) Prior Publication Data
US 2015/0284703 A1    Oct. 8, 2015

Related U.S. Application Data

(60) Provisional application No. 61/712,913, filed on Oct. 12, 2012.

(51) Int. Cl.
| | |
|---|---|
| *A61K 38/51* | (2006.01) |
| *C11D 3/48* | (2006.01) |
| *C12N 9/88* | (2006.01) |
| *C12P 19/02* | (2006.01) |
| *A01N 63/00* | (2006.01) |
| *C11D 3/386* | (2006.01) |
| *A61K 38/00* | (2006.01) |

(52) U.S. Cl.
CPC .............. *C12N 9/88* (2013.01); *A01N 63/00* (2013.01); *C11D 3/38636* (2013.01); *C12P 19/02* (2013.01); *A61K 38/00* (2013.01); *C12Y 402/02* (2013.01); *C12Y 402/02001* (2013.01); *C12Y 402/02003* (2013.01); *C12Y 402/02014* (2013.01); *Y02P 20/52* (2015.11)

(58) Field of Classification Search
CPC ................................ A61K 38/51; C11D 3/48
USPC .......................................... 435/183; 514/12.1
See application file for complete search history.

(56) References Cited

U.S. PATENT DOCUMENTS

| | | | |
|---|---|---|---|
| 4,524,137 A | 6/1985 | Hagerdal et al. | |
| 4,562,151 A | 12/1985 | Kishore | |
| 4,970,156 A | 11/1990 | Avrameas et al. | |
| 5,139,945 A | 8/1992 | Liu | |
| 5,405,414 A | 4/1995 | Pedersen et al. | |
| 5,460,957 A | 10/1995 | Hiura et al. | |
| 5,516,666 A | 5/1996 | Nozomi et al. | |
| 5,582,825 A | 12/1996 | Sakaguchi et al. | |
| 6,207,438 B1 | 3/2001 | Gedouin et al. | |
| 6,258,366 B1 | 7/2001 | Gedouin et al. | |
| 6,830,745 B1 | 12/2004 | Budny et al. | |
| 7,175,430 B1 | 2/2007 | Gasser et al. | |
| 7,273,745 B2 | 9/2007 | Andersen et al. | |
| 7,758,856 B2 | 7/2010 | Hughes et al. | |
| 8,293,226 B1 | 10/2012 | Basu et al. | |
| 8,680,072 B2 * | 3/2014 | Onsoyen | 514/54 |
| 2010/0080788 A1 | 4/2010 | Barnett et al. | |

FOREIGN PATENT DOCUMENTS

| | | |
|---|---|---|
| EP | 0979301 B1 | 9/2004 |
| WO | WO/2006/037568 | 4/2006 |
| WO | WO2008/051245 | 5/2008 |
| WO | WO/2009/042950 | 4/2009 |
| WO | WO2010/098585 | 9/2010 |
| WO | WO2012/021558 | 2/2012 |

OTHER PUBLICATIONS

Murphy et al., UniProt database, accession No. J7V1Q6, Oct. 31, 2012.*
International Search Report dated Jan. 6, 2014; International Application No. PCT/US2013/064604; International Filing Date: Oct. 11, 2013; 7 pages.
Written Opinion dated Jan. 6, 2014; International Application No. PCT/US2013/064604; International. Filing Date: Oct. 11, 2013; 11 pages.
Kim et al.; "Alginate Lyase: Structure, Property, and Application"; The Korean Society for Biotechnology and Bioengineering and Springer 2011 Biotechnology and Bioprocess Engineering; vol. 16; pp. 843-851 (2011); 9 pages.
Crossman et al.; "The complete genome, comparative and functional analysis of Stenotrophomonas maltophilia reveals an organism heavily shielded by drug resistance determinants"; Genome Biology 2008; vol. 9:R74; published Apr. 17, 2008; 13 pages.

* cited by examiner

*Primary Examiner* — Maryam Monshipouri
(74) *Attorney, Agent, or Firm* — Blank Rome LLP

(57) ABSTRACT

Described herein are proteins having lyase activity and nucleic acid sequences which code therefor; along with methods of expressing, isolating, purifying, and using same.

13 Claims, 1 Drawing Sheet

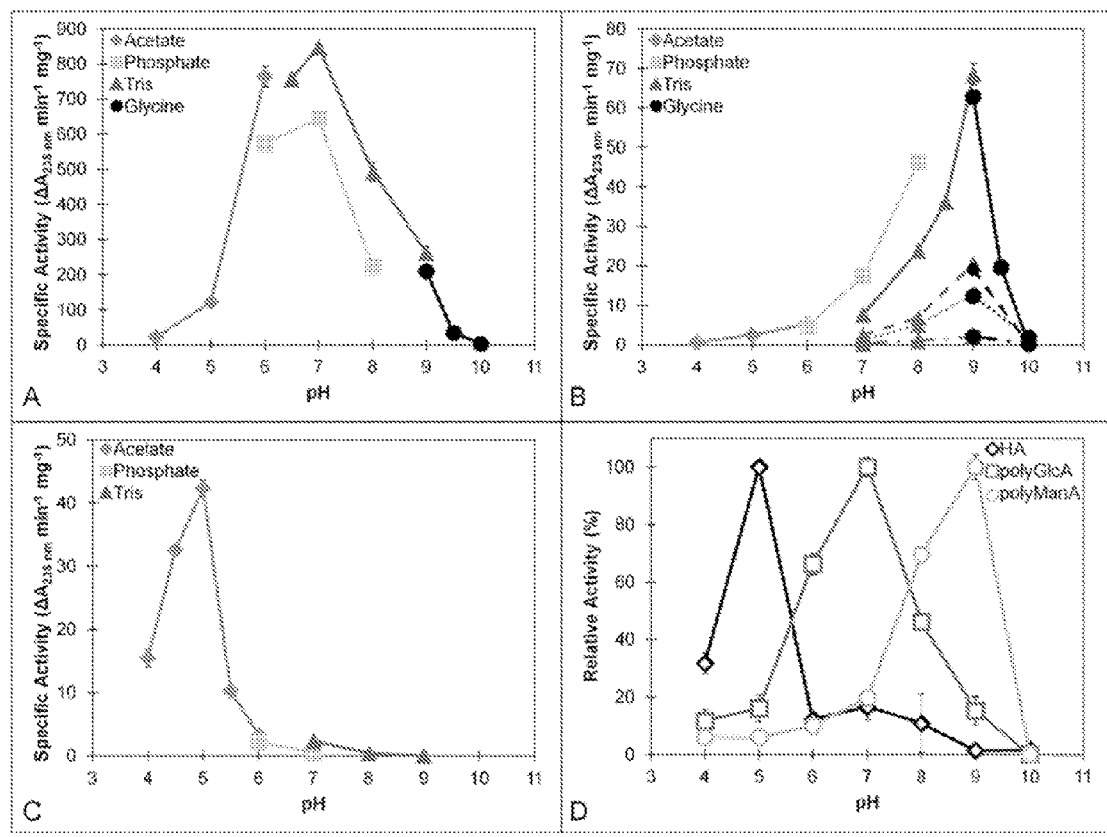

SEQUENCE LISTING

<160> NUMBER OF SEQ ID NOS: 7

<210> SEQ ID NO 1
<211> LENGTH: 1005
<212> TYPE: DNA
<213> ORGANISM: Stenotrophomonas maltophilia

<400> SEQUENCE: 1

```
atgggatcct ctctgccgct gcgcctggct ctgctgccga ccctgctggc ttccgcttcc      60
gcttttgccg cttgtccggc tccgccgccg ggccagccgg atattcgtgc aatcggctat     120
tacaccgaca aagctggtag cgttattgat ccggcgctgc agcaacagaa caaggatgcg     180 accgcccgc tggaccgtta tgccgcagat gtcgcgcgta tgtcagatga ctacctgcgc      240
aatggcgatc cggcagctgc ccagtgtacc ctgagctggc tgggtgcatg ggcagatgat     300
ggtgccatgc tgggtcagat gattcgtgtc aacaatgacc aatctttta tgcgccag       360 tggatgctgg atgctgtggc gatggcctac ctgaaagttc atgaccaggc caacccgcaa     420
cagcgcgcac gtatcgatcc gtggctgcaa aaactggcac gtgctaacct ggcgtattgg     480
gataatccga agcgtcgccg taacaatcat tattattggg gtggtctggg tgttctggcc     540
accggtctgg caaccgatga cgatgcactg tggcaagctg gccacgccgc attccagaag     600
ggtattgacg atatccaaga cgatggctcc ctgccgctgg aaatggcgcg cggtcagcgt     660
gccctgcatt atcacgatta cgcgctggcc ccgctggtga tgatggcaga actggctcgc     720
ctgcgtggcc aggactggta tgcaagtcgc aaccatgcta ttgatcgtct ggcgcgccgt     780
gttatcgaag gttcccgcga tccggcctgg tttaatcagc ataccggtgc tgcccaactg     840
```

```
ccgctgcagg caagcggttg ggtcgaattt taccgcctgc gttctccgga cggcggtgtg    900
tttgatgccg cacatgcccg tggcccgttc cacagcccgc gcctgggtgg tgacctgacg    960
ctgatggcaa cgcacggtat tgttcgcacg ccgctgcgcc tcgag                    1005
```

<210> SEQ ID NO 2
<211> LENGTH: 331
<212> TYPE: PRT
<213> ORGANISM: Stenotrophomonas maltophilia

<400> SEQUENCE: 2

```
Met Ser Leu Pro Leu Arg Leu Ala Leu Leu Pro Thr Leu Leu Ala Ser
1               5                   10                  15

Ala Ser Ala Phe Ala Ala Cys Pro Ala Pro Pro Gly Gln Pro Asp
                20                  25                  30

Ile Arg Ala Ile Gly Tyr Tyr Thr Asp Lys Ala Gly Ser Val Ile Asp
            35                  40                  45

Pro Ala Leu Gln Gln Gln Asn Lys Asp Ala Thr Ala Pro Leu Asp Arg
    50                  55                  60

Tyr Ala Ala Asp Val Ala Arg Met Ser Asp Asp Tyr Leu Arg Asn Gly
65                  70                  75                  80

Asp Pro Ala Ala Ala Gln Cys Thr Leu Ser Trp Leu Gly Ala Trp Ala
                85                  90                  95

Asp Asp Gly Ala Met Leu Gly Gln Met Ile Arg Val Asn Asn Asp Gln
            100                 105                 110

Ser Phe Tyr Met Arg Gln Trp Met Leu Asp Ala Val Ala Met Ala Tyr
        115                 120                 125

Leu Lys Val His Asp Gln Ala Asn Pro Gln Gln Arg Ala Arg Ile Asp
    130                 135                 140

Pro Trp Leu Gln Lys Leu Ala Arg Ala Asn Leu Ala Tyr Trp Asp Asn
145                 150                 155                 160

Pro Lys Arg Arg Arg Asn Asn His Tyr Tyr Trp Gly Gly Leu Gly Val
                165                 170                 175

Leu Ala Thr Gly Leu Ala Thr Asp Asp Ala Leu Trp Gln Ala Gly
            180                 185                 190

His Ala Ala Phe Gln Lys Gly Ile Asp Asp Ile Gln Asp Asp Gly Ser
        195                 200                 205

Leu Pro Leu Glu Met Ala Arg Gly Gln Arg Ala Leu His Tyr His Asp
    210                 215                 220

Tyr Ala Leu Ala Pro Leu Val Met Met Ala Glu Leu Ala Arg Leu Arg
225                 230                 235                 240

Gly Gln Asp Trp Tyr Ala Ser Arg Asn His Ala Ile Asp Arg Leu Ala
                245                 250                 255

Arg Arg Val Ile Glu Gly Ser Arg Asp Pro Ala Trp Phe Asn Gln His
            260                 265                 270

Thr Gly Ala Ala Gln Leu Pro Leu Gln Ala Ser Gly Trp Val Glu Phe
        275                 280                 285

Tyr Arg Leu Arg Ser Pro Asp Gly Gly Val Phe Asp Ala Ala His Ala
    290                 295                 300

Arg Gly Pro Phe His Ser Pro Arg Leu Gly Gly Asp Leu Thr Leu Met
305                 310                 315                 320

Ala Thr His Gly Ile Val Arg Thr Pro Leu Arg
                325                 330
```

<210> SEQ ID NO 3
<211> LENGTH: 331
<212> TYPE: PRT
<213> ORGANISM: Stenotrophomonas maltophilia

<400> SEQUENCE: 3

Met Ser Leu Pro Leu Arg Leu Ala Leu Leu Pro Thr Leu Leu Ala Ser
1               5                   10                  15

Ala Ser Ala Phe Ala Ala Cys Pro Ala Pro Pro Gly Gln Pro Asp
            20                  25                  30

Ile Arg Ala Ile Gly Tyr Tyr Thr Asp Lys Ala Gly Ser Val Ile Asp
            35                  40                  45

Pro Ala Leu Gln Gln Gln Asn Lys Asp Ala Thr Ala Pro Leu Asp Arg
        50                  55                  60

Tyr Ala Ala Asp Val Ala Arg Met Ser Asp Asp Tyr Leu Arg Asn Gly
65                  70                  75                  80

Asp Pro Ala Ala Ala Gln Cys Thr Leu Ser Trp Leu Gly Ala Trp Ala
                85                  90                  95

Asp Asp Gly Ala Met Leu Gly Gln Met Ile Arg Val Asn Asn Asp Gln
            100                 105                 110

Ser Phe Phe Met Arg Gln Trp Met Leu Asp Ala Val Ala Met Ala Tyr
        115                 120                 125

Leu Lys Val His Asp Gln Ala Asn Pro Gln Gln Arg Ala Arg Ile Asp
130                 135                 140

Pro Trp Leu Gln Lys Leu Ala Arg Ala Asn Leu Ala Tyr Trp Asp Asn
145                 150                 155                 160

Pro Lys Arg Arg Arg Asn Asn His Tyr Tyr Trp Gly Gly Leu Gly Val
                165                 170                 175

Leu Ala Thr Gly Leu Ala Thr Asp Asp Asp Ala Leu Trp Gln Ala Gly
            180                 185                 190

His Ala Ala Phe Gln Lys Gly Ile Asp Asp Ile Gln Asp Asp Gly Ser
        195                 200                 205

Leu Pro Leu Glu Met Ala Arg Gly Gln Arg Ala Leu His Tyr His Asp
    210                 215                 220

Tyr Ala Leu Ala Pro Leu Val Met Met Ala Glu Leu Ala Arg Leu Arg
225                 230                 235                 240

Gly Gln Asp Trp Tyr Ala Ser Arg Asn His Ala Ile Asp Arg Leu Ala
                245                 250                 255

Arg Arg Val Ile Glu Gly Ser Arg Asp Pro Ala Trp Phe Asn Gln His
            260                 265                 270

Thr Gly Ala Ala Gln Leu Pro Leu Gln Ala Ser Gly Trp Val Glu Phe
        275                 280                 285

Tyr Arg Leu Arg Ser Pro Asp Gly Gly Val Phe Asp Ala Ala His Ala
    290                 295                 300

Arg Gly Pro Phe His Ser Pro Arg Leu Gly Gly Asp Leu Thr Leu Met
305                 310                 315                 320

Ala Thr His Gly Ile Val Arg Thr Pro Leu Arg
                325                 330

<210> SEQ ID NO 4
<211> LENGTH: 331
<212> TYPE: PRT
<213> ORGANISM: Stenotrophomonas maltophilia

<400> SEQUENCE: 4

Met Ser Leu Pro Leu Arg Leu Ala Leu Leu Pro Thr Leu Leu Ala Ser

```
            1               5                  10                 15
Ala Ser Ala Phe Ala Ala Cys Pro Ala Pro Pro Gly Gln Pro Asp
                20                  25                 30

Ile Arg Ala Ile Gly Tyr Tyr Thr Asp Lys Ala Gly Ser Val Ile Asp
                35                  40                 45

Pro Ala Leu Gln Gln Gln Asn Lys Asp Ala Thr Ala Pro Leu Asp Arg
 50                 55                  60

Tyr Ala Ala Asp Val Ala Arg Met Ser Asp Asp Tyr Leu Arg Asn Gly
 65                 70                  75                 80

Asp Pro Ala Ala Ala Gln Cys Thr Leu Ser Trp Leu Gly Ala Trp Ala
                85                  90                 95

Asp Asp Gly Ala Met Leu Gly Gln Met Ile Arg Val Asn Asn Asp Gln
                100                 105                110

Ser Phe Tyr Met Arg Gln Trp Met Leu Asp Ala Val Ala Met Ala Tyr
                115                 120                125

Leu Lys Val His Asp Gln Ala Asn Pro Gln Gln Arg Ala Arg Ile Asp
                130                 135                140

Pro Trp Leu Gln Lys Leu Ala Arg Ala Asn Leu Ala Tyr Trp Asp Asn
145                 150                 155                160

Pro Lys Arg Arg Arg Asn Asn His Tyr Tyr Ala Gly Gly Leu Gly Val
                165                 170                175

Leu Ala Thr Gly Leu Ala Thr Asp Asp Ala Leu Trp Gln Ala Gly
                180                 185                190

His Ala Ala Phe Gln Lys Gly Ile Asp Asp Ile Gln Asp Asp Gly Ser
                195                 200                205

Leu Pro Leu Glu Met Ala Arg Gly Gln Arg Ala Leu His Tyr His Asp
 210                215                 220

Tyr Ala Leu Ala Pro Leu Val Met Met Ala Glu Leu Ala Arg Leu Arg
225                 230                 235                240

Gly Gln Asp Trp Tyr Ala Ser Arg Asn His Ala Ile Asp Arg Leu Ala
                245                 250                255

Arg Arg Val Ile Glu Gly Ser Arg Asp Pro Ala Trp Phe Asn Gln His
                260                 265                270

Thr Gly Ala Ala Gln Leu Pro Leu Gln Ala Ser Gly Trp Val Glu Phe
                275                 280                285

Tyr Arg Leu Arg Ser Pro Asp Gly Gly Val Phe Asp Ala Ala His Ala
                290                 295                300

Arg Gly Pro Phe His Ser Pro Arg Leu Gly Gly Asp Leu Thr Leu Met
305                 310                 315                320

Ala Thr His Gly Ile Val Arg Thr Pro Leu Arg
                325                 330

<210> SEQ ID NO 5
<211> LENGTH: 331
<212> TYPE: PRT
<213> ORGANISM: Stenotrophomonas maltophilia

<400> SEQUENCE: 5

Met Ser Leu Pro Leu Arg Leu Ala Leu Leu Pro Thr Leu Leu Ala Ser
 1               5                  10                 15

Ala Ser Ala Phe Ala Ala Cys Pro Ala Pro Pro Gly Gln Pro Asp
                20                  25                 30

Ile Arg Ala Ile Gly Tyr Tyr Thr Asp Lys Ala Gly Ser Val Ile Asp
                35                  40                 45
```

```
Pro Ala Leu Gln Gln Gln Asn Lys Asp Ala Thr Ala Pro Leu Asp Arg
    50                  55                  60

Tyr Ala Ala Asp Val Ala Arg Met Ser Asp Asp Tyr Leu Arg Asn Gly
65                  70                  75                  80

Asp Pro Ala Ala Ala Gln Cys Thr Leu Ser Trp Leu Gly Ala Trp Ala
                85                  90                  95

Asp Asp Gly Ala Met Leu Gly Gln Met Ile Arg Val Asn Asn Asp Gln
            100                 105                 110

Ser Phe Tyr Met Arg Gln Trp Met Leu Asp Ala Val Ala Met Ala Tyr
            115                 120                 125

Leu Lys Val His Asp Gln Ala Asn Pro Gln Gln Arg Ala Arg Ile Asp
        130                 135                 140

Pro Trp Leu Gln Lys Leu Ala Arg Ala Asn Leu Ala Tyr Trp Asp Asn
145                 150                 155                 160

Pro Lys Arg Arg Arg Asn Asn His Tyr Tyr Trp Gly Gly Leu Gly Val
                165                 170                 175

Leu Ala Thr Gly Leu Ala Thr Asp Asp Ala Leu Trp Gln Ala Gly
            180                 185                 190

His Ala Ala Phe Gln Lys Gly Ile Asp Ile Gln Asp Asp Gly Ser
        195                 200                 205

Leu Pro Leu Glu Met Ala Arg Gly Gln Arg Ala Leu Phe Tyr His Asp
    210                 215                 220

Tyr Ala Leu Ala Pro Leu Val Met Met Ala Glu Leu Ala Arg Leu Arg
225                 230                 235                 240

Gly Gln Asp Trp Tyr Ala Ser Arg Asn His Ala Ile Asp Arg Leu Ala
                245                 250                 255

Arg Arg Val Ile Glu Gly Ser Arg Asp Pro Ala Trp Phe Asn Gln His
            260                 265                 270

Thr Gly Ala Ala Gln Leu Pro Leu Gln Ala Ser Gly Trp Val Glu Phe
        275                 280                 285

Tyr Arg Leu Arg Ser Pro Asp Gly Gly Val Phe Asp Ala Ala His Ala
    290                 295                 300

Arg Gly Pro Phe His Ser Pro Arg Leu Gly Gly Asp Leu Thr Leu Met
305                 310                 315                 320

Ala Thr His Gly Ile Val Arg Thr Pro Leu Arg
                325                 330

<210> SEQ ID NO 6
<211> LENGTH: 331
<212> TYPE: PRT
<213> ORGANISM: Stenotrophomonas maltophilia

<400> SEQUENCE: 6

Met Ser Leu Pro Leu Arg Leu Ala Leu Leu Pro Thr Leu Leu Ala Ser
1               5                   10                  15

Ala Ser Ala Phe Ala Ala Cys Pro Ala Pro Pro Gly Gln Pro Asp
            20                  25                  30

Ile Arg Ala Ile Gly Tyr Tyr Thr Asp Lys Ala Gly Ser Val Ile Asp
        35                  40                  45

Pro Ala Leu Gln Gln Gln Asn Lys Asp Ala Thr Ala Pro Leu Asp Arg
    50                  55                  60

Tyr Ala Ala Asp Val Ala Arg Met Ser Asp Asp Tyr Leu Arg Asn Gly
65                  70                  75                  80

Asp Pro Ala Ala Ala Gln Cys Thr Leu Ser Trp Leu Gly Ala Trp Ala
                85                  90                  95
```

Asp Asp Gly Ala Met Leu Gly Gln Met Ile Arg Val Asn Asn Asp Gln
            100                 105                 110

Ser Phe Tyr Met Arg Gln Trp Met Leu Asp Ala Val Ala Met Ala Tyr
            115                 120                 125

Leu Lys Val His Asp Gln Ala Asn Pro Gln Gln Arg Ala Arg Ile Asp
            130                 135                 140

Pro Trp Leu Gln Lys Leu Ala Arg Ala Asn Leu Ala Tyr Trp Asp Asn
145                 150                 155                 160

Pro Lys Arg Arg Asn Asn His Tyr Tyr Trp Gly Gly Leu Gly Val
            165                 170                 175

Leu Ala Thr Gly Leu Ala Thr Asp Asp Ala Leu Trp Gln Ala Gly
            180                 185                 190

His Ala Ala Phe Gln Lys Gly Ile Asp Asp Ile Gln Asp Asp Gly Ser
            195                 200                 205

Leu Pro Leu Glu Met Ala Arg Gly Gln Arg Ala Leu His Tyr His Asp
            210                 215                 220

Phe Ala Leu Ala Pro Leu Val Met Met Ala Glu Leu Ala Arg Leu Arg
225                 230                 235                 240

Gly Gln Asp Trp Tyr Ala Ser Arg Asn His Ala Ile Asp Arg Leu Ala
            245                 250                 255

Arg Arg Val Ile Glu Gly Ser Arg Asp Pro Ala Trp Phe Asn Gln His
            260                 265                 270

Thr Gly Ala Ala Gln Leu Pro Leu Gln Ala Ser Gly Trp Val Glu Phe
            275                 280                 285

Tyr Arg Leu Arg Ser Pro Asp Gly Gly Val Phe Asp Ala Ala His Ala
            290                 295                 300

Arg Gly Pro Phe His Ser Pro Arg Leu Gly Gly Asp Leu Thr Leu Met
305                 310                 315                 320

Ala Thr His Gly Ile Val Arg Thr Pro Leu Arg
            325                 330

<210> SEQ ID NO 7
<211> LENGTH: 331
<212> TYPE: PRT
<213> ORGANISM: Stenotrophomonas maltophilia

<400> SEQUENCE: 7

Met Ser Leu Pro Leu Arg Leu Ala Leu Leu Pro Thr Leu Leu Ala Ser
1               5                   10                  15

Ala Ser Ala Phe Ala Ala Cys Pro Ala Pro Pro Gly Gln Pro Asp
            20                  25                  30

Ile Arg Ala Ile Gly Tyr Tyr Thr Asp Lys Ala Gly Ser Val Ile Asp
            35                  40                  45

Pro Ala Leu Gln Gln Gln Asn Lys Asp Ala Thr Ala Pro Leu Asp Arg
50                  55                  60

Tyr Ala Ala Asp Val Ala Arg Met Ser Asp Asp Tyr Leu Arg Asn Gly
65                  70                  75                  80

Asp Pro Ala Ala Ala Gln Cys Thr Leu Ser Trp Leu Gly Ala Trp Ala
            85                  90                  95

Asp Asp Gly Ala Met Leu Gly Gln Met Ile Arg Val Asn Asn Asp Gln
            100                 105                 110

Ser Phe Tyr Met Arg Gln Trp Met Leu Asp Ala Val Ala Met Ala Tyr
            115                 120                 125

Leu Lys Val His Asp Gln Ala Asn Pro Gln Gln Arg Ala Arg Ile Asp

-continued

```
                130                 135                 140
Pro Trp Leu Gln Lys Leu Ala Arg Ala Asn Leu Ala Tyr Trp Asp Asn
145                 150                 155                 160

Pro Lys Arg Arg Arg Asn Leu His Tyr Tyr Trp Gly Gly Leu Gly Val
                165                 170                 175

Leu Ala Thr Gly Leu Ala Thr Asp Asp Asp Ala Leu Trp Gln Ala Gly
                180                 185                 190

His Ala Ala Phe Gln Lys Gly Ile Asp Asp Ile Gln Asp Asp Gly Ser
                195                 200                 205

Leu Pro Leu Glu Met Ala Arg Gly Gln Arg Ala Leu His Tyr His Asp
                210                 215                 220

Tyr Ala Leu Ala Pro Leu Val Met Met Ala Glu Leu Ala Arg Leu Arg
225                 230                 235                 240

Gly Gln Asp Trp Tyr Ala Ser Arg Asn His Ala Ile Asp Arg Leu Ala
                245                 250                 255

Arg Arg Val Ile Glu Gly Ser Arg Asp Pro Ala Trp Phe Asn Gln His
                260                 265                 270

Thr Gly Ala Ala Gln Leu Pro Leu Gln Ala Ser Gly Trp Val Glu Phe
                275                 280                 285

Tyr Arg Leu Arg Ser Pro Asp Gly Gly Val Phe Asp Ala Ala His Ala
                290                 295                 300

Arg Gly Pro Phe His Ser Pro Arg Leu Gly Gly Asp Leu Thr Leu Met
305                 310                 315                 320

Ala Thr His Gly Ile Val Arg Thr Pro Leu Arg
                325                 330
```

THERMALLY STABLE ENZYMES, COMPOSITIONS THEREOF AND METHODS OF USING SAME

CROSS-REFERENCE TO RELATED APPLICATION

The present application is a U.S. National Stage Application under 35 U.S.C. §371 of PCT Application No. PCT/US2013/064604, filed 11 Oct. 2013, which in turn claims the benefit of U.S. Provisional Application Ser. No. 61/712,913, filed 12 Oct. 2012, entitled "Thermally Stable Alginate Lyase", the entireties of which are hereby incorporated by reference herein.

BACKGROUND

Polysaccharide lyases degrade anionic polysaccharides that are important in bacterial biofilm formation and host-pathogen interactions.

Stenotrophomonas maltophilia is a ubiquitous, gram-negative bacteria that has become an increasingly important nosocomial pathogen in immunocompromised patients. Approximately 1% of all nosocomial bacteraemias are due to S. maltophilia infection, with the attributed mortality rate at nearly 28%, which places it among the highest attributed mortality rates observed for nosocomal bacteraemias. A major reason for the high mortality associated with S. maltophilia is its nearly universal resistance to broad-spectrum antibiotics such as imipenem and aminoglycosides, and increasing resistance to 'last-line' cephelasporin antibiotics such as ceftazidime and cefotaxime.

One unique mechanism that S. maltophilia has evolved to become multi-drug resistant (MDR) is its production of highly branched, anionic exopolysaccharides (EPS) to form biofilms. Biofilms are comprised of secreted, high molecular weight EPS such as alginic acid, which encapsulate a population of bacterial cells to create a 'niche' environment that is often impermeable to antimicrobials, detergents or other organic compounds.

While several pathogenic bacteria are capable of producing alginic acid biofilms, S. maltophilia is unique in that the EPS that comprise the biofilm are highly anionic due to the addition of branched poly-D-galacturonic acid (HexA)-ethyl-D-lactate (Lac) chains. Recent studies indicate the additional negative charge of S. maltophilia EPS due to the branched HexA-Lac group enables biofilm binding to metallic or plastic surfaces, as well as creating, a heat-, acid- and detergent-resistant environment that allows S. maltophilia to colonize water purification systems, ventilators and stents. As a result, S. maltophilia is the $2^{nd}$ leading cause of ventilator-associated pneumonia, with over 70% of all S. maltophilia-specific, ventilator associated MDR infections caused by biofilm forming strains.

In biofilm-positive MDR infections, surgery is the main option to either remove infected lung tissue or perform a lung transplant, although both are often not feasible since the patient is immunocompromised and therefore at greater risk of additional infections. This is especially a problem for cystic fibrosis (CF) patients, in which accumulation of mucin in the lungs creates a viscous, damp environment in which biofilm-producing S. maltophilia can thrive. S. maltophilia is the $2^{nd}$ most common cause of chronic infection in CF patients after P. aeruginosa, with estimates as high as 20% of all MDR infections. Thus, biofilm formation plays a central role in the pathogenicity of S. maltophilia, and strategies targeting. EPS degradation will enable more effective treatments to prevent chronic. S. maltophilia infection, particularly in CF and immunocompromised patients.

Embodiments of the present invention are directed to these and other ends.

SUMMARY

In some embodiments, the present invention provides a protein comprising an amino sequence selected from SEQ ID NO: 2; SEQ ID NO: 3; SEQ ID NO 4; SEQ ID NO: 5; SEQ ID NO: 6; and SEQ ID NO: 7.

In some embodiments, the present invention provides a protein comprising an amino acid sequence having at least 75% sequence identity to SEQ ID NO: 2; SEQ ID NO: 3; SEQ ID NO: 4; SEQ ID NO: 5; SEQ ID NO: 6; or SEQ ID NO: 7.

Some embodiments of the present invention provide a composition comprising: a protein comprising an amino sequence selected from SEQ ID NO: 2; SEC ID NO: 3; SEQ ID NO: 4; SEQ ID NO 5; SEQ ID NO: 6; and SEQ ID NO: 7; and a carrier.

Other embodiments of the present invention provide a protein having a signature motif that aligns with a reference sequence SEQ ID NO: 2, wherein the signature motif comprises N167, H168, R215, Y222 residues.

In some embodiments, the present invention provides methods of preventing, treating or inhibiting a disease, disorder or condition selected from: a urinary tract infection, a catheter-originated infection, a middle-ear infection, dental plaque, gingivitis, an eye infection, endocarditis, cystic fibrosis, and nosocomial infections, comprising administering an effective amount of a composition comprising an amino acid sequence selected from SEQ ID NO: 2; SEQ ID NO: 3; SEQ ID NO: 4; SEQ ID NO: 5; SEQ ID NO: 6; and SEQ ID NO: 7, to a patient in need thereof.

Still further embodiments of the present invention provide methods of cleaning, disinfecting or sterilizing an inert surface. In some embodiments, the inert surface is selected from a prosthetic device, a ventilator, a catheter and an intrauterine device.

Yet further embodiments, provide methods of producing a biofuel comprising contacting a hydrolysate with an effective amount of a protein comprising an amino acid sequence selected from SEQ ID NO: 2; SEQ ID NO: 3; SEQ ID NO: 4; SEQ ID NO: 5; SEQ ID NO: 6; and SEQ ID NO: 7.

BRIEF DESCRIPTION OF THE BIOLOGICAL SEQUENCES

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO: 1 is the codon-optimized nucleotide sequence of a polysaccharide lyase from Stenotrophomonas maltophilia (Smlt1473).

SEQ ID NO: 2 is the amino acid sequence of a polysaccharide lyase from Stenotrophomonas maltophilia.

SEQ ID NO: 3 is the amino acid sequence of a Y115F mutant of SEQ ID NO: 2.

SEQ ID NO: 4 is the amino acid sequence of a W171A mutant of SEQ ID NO: 2.

SEQ ID NO: 5 is the amino acid sequence of a H221F mutant of SEQ ID NO: 2.

SEQ ID NO: 6 is the amino acid sequence of a Y225F mutant of SEQ ID NO: 2.

SEQ ID NO: 7 is the amino acid sequence of a N167L mutant of SEQ ID NO: 2.

BRIEF DESCRIPTION OF THE DRAWING

FIG. 1 (A-D) depicts the pH dependent activity of an exemplary protein of the present invention, against various substrates.

DETAILED DESCRIPTION

As used herein, "contacting" refers to placing a composition in contact with the target body surface for a period of time sufficient to achieve the desired result. In some embodiments, "contacting" may refer to placing a composition comprising (or capable of producing) an efficacious concentration of a lyase, as described herein, in contact with a target body surface for a period of time sufficient to achieve the desired result. Contacting includes spraying, treating, immersing, flushing, pouring on or in, mixing, combining, painting, coating, applying, affixing to and otherwise communicating a lyase solution or a composition comprising an efficacious concentration of lyase, a solution or composition that forms an efficacious concentration of lyase or a component of the composition that forms an efficacious concentration of lyase with the body surface.

As used herein, an "isolated nucleic acid molecule", "isolated polynucleotide", and "isolated nucleic acid fragment" may be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "amino acid" refers to the basic chemical structural unit of a protein or polypeptide. Table 1 (below) provides a list of abbreviations used herein to identify specific amino acids:

TABLE 1

| Amino Acid | Three-letter Abbreviation | One-letter Abbreviation |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

It is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, lie, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

As used herein, the terms "signature motif" and "diagnostic motif" refer to conserved structures shared among a family of enzymes having a defined activity. The signature motif can be used to define and/or identify the family of structurally-related enzymes having similar enzymatic activity for certain substrates. The signature motif can be a single contiguous amino acid sequence or a collection of discontiguous, conserved, motifs or residues that together form the signature motif.

As used herein, the term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes. As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene.

As used herein, the term "chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "pharmaceutically-acceptable" means that drugs, medicaments and/or inert ingredients which the term describes are suitable for use in contact with the tissues of humans and other animals without undue toxicity, incompatibility, instability, irritation, allergic response, and the like, commensurate with a reasonable benefit/risk ratio.

As used herein, the terms "pharmaceutically acceptable carrier", "orally acceptable carrier" and "cosmetically acceptable carrier" may have overlapping scope. However, one skilled in the art would appreciate that some ingredients suitable for use in a "pharmaceutically acceptable carrier" or a "cosmetically acceptable carrier" may not be suitable for use in an "orally acceptable carrier".

Compositions envisioned by the present application include oral care compositions, personal care compositions (e.g., skin care, hair care and ocular compositions), and pharmaceutical compositions (topical and systemic).

As used herein, the term "oral care composition" refers to a composition for which the intended use can include oral care, oral hygiene, or oral appearance, or for which the intended method of use can comprise administration to the oral cavity.

As used herein, an "orally acceptable carrier" and "orally acceptable vehicle" are used interchangeably, and refer to a material or combination of materials that is safe for use in the oral cavity, commensurate with a reasonable benefit/risk, ratio, with which the other ingredients may be associated while retaining efficacy. Such carrier materials should be selected for compatibility with the other ingredients of the compositions, and preferably do not substantially reduce the efficacy of the other ingredients. Selection of specific carrier components is dependent on the desired product form, including dentifrices, rinses, gels, and paints.

Materials useful in an "orally acceptable carrier" include, but are not limited to: adhesion agents, viscosity modifiers, diluents, surfactants, foam modulators, peroxide activators, peroxide stability agents, abrasives, pH modifying agents, humectants, mouth feel agents, sweeteners, flavorants, colorants, and combinations thereof.

As used herein, an "adhesion agent" is a material or combination of materials that enhances the retention of an ingredient to an oral cavity surface onto which it is applied. Such adhesion agents include without limitation: adhesives, film forming materials and viscosity enhancers; for example, hydrophilic organic polymers, hydrophobic organic polymers, silicone gums, silicone adhesives, silicas, and combinations thereof.

As used herein, the term "personal care composition" refers to a composition for which the intended use can include promotion or improvement of health, cleanliness, odor, appearance, or attractiveness of skin.

Materials useful in a "cosmetically acceptable carrier" include, but are not limited to an ingredient selected from a surfactant, a conditioning agent, a moisturizer, an enzyme or other protein, a vitamin, a colorant, a denaturant, a film forming polymer, an antidandruff agent, to fragrance, an alcohol, an anticholinergic, an antiperspirant salt (such as aluminum and zirconium salts).

The compositions described herein may be adapted for oral, parenteral, sublingual, nasal or transdermal administration. The compositions may be in the form of tablets, capsules, powders, granules, lozenges, suppositories, reconstitutable powders, or liquid preparations, such as oral or sterile parenteral solutions or suspensions.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine, tabletting lubricants, for example magnesia stearate; disintegrants, for example starch, polyvinylpyrrolidone, sodium starch glycollate or microcrystalline cellulose; or pharmaceutically acceptable wetting agents such as sodium lauryl sulphate.

In some embodiments, suitable lyases may include enzymes comprising an amino acid sequence having at least 30%, 33%, 40%, 50%, 60%, 70%, 80%, 85%, 90%, 91%, 92%, 93%, 94%, 95%, 96%, 97%, 98%, or 99% sequence identity to any of the amino acid sequences reported herein.

In some embodiments, suitable isolated nucleic acid molecules encode a protein having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to the amino acid sequences reported herein. Suitable nucleic acid molecules not only have the above homologies, but also typically encode a protein having about 210 to 380 amino acids in length, about 300 to about 360 amino acids, preferably about 310 to about 350 amino acids, and most preferably about 320 to about 335 amino acids in length wherein each protein is characterized as having lyase activity.

As used herein, the term "body surface" refers to any surface of the human body that may serve as the target for a lyase benefit agent. In some embodiments, the proteins described herein have an affinity for a particular body surface.

As used herein, the term "effective amount" refers to the quantity of an amino acid sequence or composition necessary to achieve the enzymatic activity required in the specific application. Such effective amounts are readily ascertained by one of ordinary skill in the art and are based on many factors, such as the particular enzyme variant used, the intended use or application, the specific composition for the intended use or application, and the dosage form in which the enzyme is prepared (e.g. solid, liquid, etc.).

As used herein, the term "mutant" or "variant" refers to an enzyme having a genetic modification that results in at least one amino acid addition, deletion, and/or substitution when compared to the corresponding enzyme (typically the wild type enzyme) from which the variant was derived; so long as the signature motif and the associated lyase activity are maintained. Examples of variants are provided as SEQ ID NOs: 3, 4, 5, 6, and 7.

As the skilled artisan will recognize, substantially similar sequences (retaining the signature motifs) to those described herein may also be used in the present compositions and methods. In some embodiments, the substantially similar sequences are defined by their ability to hybridize, under highly stringent conditions with the nucleic acid molecules associated with sequences exemplified herein. In some embodiments, sequence alignment algorithms may be used to define substantially similar enzymes based on the percent identity to the nucleotide or amino acid sequences provided herein.

As used herein, the term "percent identity" refers to the relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" can be readily calculated by known methods, included but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed. Academic Press (1987); and *Sequence Analysis Primer* (Gribskov, M. and Devereux, J., Eds.) Stockton Press, NY (1991).

Hyaluronic acid (HA) is found in mammals predominantly in connective tissues, skin, cartilage, and in synovial fluid. Hyaluronic acid is also the main constituent of the vitreous of the eye. In connective tissue, the water of hydration associated with hyaluronic acid creates spaces between tissues, thus creating an environment conducive to cell movement and proliferation. Hyaluronic acid plays a key role in biological phenomena associated with cell motility including rapid development, regeneration, repair, embryogenesis, embryological development, wound healing, angiogenesis, and tumorigenesis (Toole 1991 Cell Biol. Extracell. Matrix, Hay (ed), Plenum Press, New York, 1384-1386; Bertrand et al. 1992 Int. J. Cancer 52:1-6; Knudson et al, 1993 FASEB J. 7:1233-1241). In addition, hyaluronic acid levels correlate with tumor aggressiveness (Ozello et al. 1960 Cancer Res. 20:600-604; Takeuchi et al. 1976, Cancer Res. 36:2133-2139: Kimata et al. 1983 Cancer Res. 43:1347-1354).

Hyaluronic acid is found in the extracellular matrix of many cells, especially in soft connective tissues. Hyaluronic acid has been assigned various physiological functions, such as in water and plasma protein homeostasis (Laurent T C et al (1992) FASEB J 6: 2397-2404). Hyaluronic acid production increases in proliferating cells and may play a role in mitosis. It has also been implicated in locomotion and cell migration. Hyaluronic acid seems to play important roles in cell regulation, development, and differentiation (Laurent et al, supra).

Hyaluronic acid has been used in clinical medicine. Its tissue protective and rheological properties have proved useful in ophthalmic surgery to protect the corneal endothelium during cataract surgery. Serum hyaluronic acid is diagnostic of liver disease and various inflammatory conditions, such as rheumatoid arthritis. Interstitial edema caused by accumulation of hyaluronic acid may cause dysfunction in various organs (Laurent et al, supra).

Some embodiments of the present invention provide a protein comprising an amino sequence selected from SEQ ID NO: 2; SEQ ID NO: 3; SEQ ID NO: 4; SEQ ID NO: 5; SEQ ID NO: 6; and SEQ ID NO: 7.

Some embodiments of the present invention provide a protein having lyase activity comprising an amino sequence selected from SEQ ID NO: 2; SEQ ID NO: 3; SEQ ID NO: 4; SEQ ID NO: 5; SEQ ID NO: 6; and SEQ ID NO: 7.

In some embodiments, the protein comprises the amino acid sequence of SEQ ID NO: 2. In some embodiments, the protein comprises the amino acid sequence of SEQ ID NO: 3. In some embodiments, the protein comprises the amino acid sequence of SEQ ID NO: 4. In some embodiments, the protein comprises the amino acid sequence of SEQ ID NO: 5. In some embodiments, the protein comprises the amino acid sequence of SEQ ID NO: 6. In some embodiments, the protein comprises the amino acid sequence of SEQ ID NO: 7.

Some embodiments of the present invention provide a protein comprising an amino acid sequence having at least 50%, 75%, 80%, 85%, 90%, 95% or 99% sequence identity to SEQ ID NO: 2.

Some embodiments of the present invention provide a protein having lyase activity comprising an amino acid sequence having at least 50%, 75%, 80%, 85%, 90%, 95% or 99% sequence identity to SEQ ID NO: 2.

Some embodiments of the present invention provide a protein comprising an amino acid sequence having at least 50%, 75%, 80%, 85%, 90%, 95% or 99% sequence identity to SEQ ID NO: 3.

Some embodiments of the present invention provide a protein having lyase activity comprising an amino acid sequence having at least 50%, 75%, 80%, 85%, 90%, 95% or 99% sequence identity to SEQ ID NO: 3.

Some embodiments of the present invention provide a protein comprising an amino acid sequence having at least 50%, 75%, 80%, 85%, 90%, 95% or 99% sequence identity to SEQ ID NO: 4.

Some embodiments of the present invention provide a protein having lyase activity comprising an amino acid sequence having at least 50%, 75%, 80%, 85%, 90%, 95% or 99% sequence identity to SEQ ID NO: 4.

Some embodiments of the present invention provide a protein comprising an amino acid sequence having at least 50%, 75%, 80%, 85%, 90%, 95% or 99% sequence identity to SEQ ID NO: 5.

Some embodiments of the present invention provide a protein having lyase activity comprising an amino acid sequence having at least 50%, 75%, 80%, 85%, 90%, 95% or 99% sequence identity to SEQ ID NO 5.

Some embodiments of the present invention provide a protein comprising an amino acid sequence having at least 50%, 75%, 80%, 85%, 90%, 95% or 99% sequence identity to SEQ ID NO: 6.

Some embodiments of the present invention provide a protein having lyase activity comprising an amino acid sequence having at least 50%, 75%, 80%, 85%, 90%, 95% or 99% sequence identity to SEQ ID NO: 6.

Some embodiments of the present invention provide a protein comprising an amino acid sequence having at least 50%, 75%, 80%, 85%, 90%, 95% or 99% sequence identity to SEQ ID NO: 7.

Some embodiments of the present invention provide a protein having lyase activity comprising an amino acid sequence having at least 50%, 75%, 80%, 85%, 90%, 95% or 99% sequence identity to SEQ ID NO 7.

Further embodiments of the present invention provide a protein comprising a signature motif comprising N167, H168, R215, Y222 residues.

Still further embodiments of the present invention provide a protein comprising a signature motif consisting essentially of N167, H168, R215, Y222 residues.

Yet further embodiments of the present invention provide a protein comprising a signature motif consisting of N167, H168, R215, Y222 residues.

Other embodiments of the present invention provide a protein having lyase activity comprising a signature motif comprising N167, H168, R215, Y222 residues.

Still other embodiments of the present invention provide a protein having lyase activity comprising a signature motif consisting essentially of N167, H168, R215, Y222 residues.

While other embodiments of the present invention provide a protein having lyase activity comprising a signature motif consisting of N167, H168, R215, Y222 residues.

Some embodiments of the present invention provide a protein having a signature motif that aligns with a reference sequence SEQ ID NO: 2, wherein the signature motif comprises N167, H168, R215, Y222 residues.

Yet other embodiments of the present invention provide a protein having lyase activity having a signature motif that aligns with a reference sequence SEQ ID NO: 2, wherein the signature motif comprises N167, H168, R215, Y222 residues.

In some embodiments, the present invention provides a composition comprising: a protein comprising an amino sequence selected from SEQ ID NO: 2; SEQ ID NO: 3; SEQ ID NO: 4; SEQ ID NO: 5; SEQ ID NO: 6; and SEQ ID NO: 7; and a carrier.

In some embodiments, the present invention provides a composition comprising: a protein having lyase activity comprising an amino sequence selected from SEQ ID NO: 2; SEQ ID NO: 3; SEQ ID NO: 4; SEQ ID NO: 5; SEQ ID NO: 6; and SEQ ID NO: 7; and a carrier.

In some embodiments, the carrier is selected from a pharmaceutically acceptable carrier; an orally acceptable carrier; and a cosmetically acceptable carrier. In some embodiments, the carrier comprises a polyol. In some embodiments, the polyol is selected from selected from a diol; a triol; and other alcohols containing multiple hydroxyl groups, and a combination of two or more thereof. In some embodiments, the polyol is selected from glycerin; glycerol; polyethylene glycol; polypropylene glycol; isomalt; lactitol; maltitol; mannitol; sorbitol; xylitol; and combination of two or more thereof in some embodiments, the polyol comprises glycerin.

In some embodiments, the carrier further comprises a chelating agent. In some embodiments, the chelating agent is selected from ethylenediaminetetraacetic acid (EDTA); citric acid phosphono-acetic acid (PAA), and nitrolotriacetic acid (NTA). In some embodiments, the chelating agent comprises a calcium chelating agent. In some embodiments, the chelating agent comprises EDTA.

In some embodiments, the carrier may comprise a detergent. In some embodiments, the detergent is selected from: octyl glycoside; lauryldimethylamine N-oxide (LDAO); n-Decyl-β-D-thiomaltoside (Anapoe $C_{10}E_6$); and a polysorbate (e.g. Tween 20).

In some embodiments of the present invention, the proteins described herein are capable of maintaining their activity at temperatures in excess of 20 deg. C. In some embodiments of the present invention, the proteins described herein are capable of maintaining their activity at temperatures in excess of 25 deg. C. In some embodiments of the present invention, the proteins described herein are capable of maintaining their activity at temperatures in excess of 30 deg. C. In some embodiments of the present invention, the proteins described, herein are capable of maintaining their activity at temperatures in excess of 35 deg. C. In some embodiments of the present invention, the proteins described herein are capable of maintaining their activity at temperatures in excess of 40 deg. C. In some embodiments of the present invention, the proteins described herein are capable of maintaining their activity at temperatures in excess of 45 deg. C. In some embodiments of the present invention, the proteins described herein are capable of maintaining their activity at temperatures in excess of 50 deg. C.

In some embodiments, the compositions described herein are formulated to maintain enzyme activity at temperatures of from about 0 deg. C. to about 70 deg. C.

In some embodiments, the compositions described herein are formulated to have pH selective activity. In some embodiments, the pH-selective activity allows the composition to target specific sites on a body surface. In some embodiments, the pH-selective activity allows the composition to target specific sites within the body.

In some embodiments, the present invention provides a nucleic acid molecule comprising SEQ ID NO: 1.

Some embodiments of the present invention provide a method of producing a biofuel comprising contacting a hydrolysate with an effective amount of a protein having lyase activity comprising an amino acid sequence selected from SEQ ID NO: 2; SEQ ID NO: 3; SEQ ID NO: 4; SEQ ID NO: 5; SEQ ID NO: 6; and SEQ ID NO: 7.

In some embodiments, the hydrolysate is derived from an extract of a seaweed selected from the group consisting of red algae, brown algae, green algae and a combination thereof. In some embodiments, the red algae comprise laver, agar-agar, sea string, and Grateloupiaceae. In some embodiments, the brown algae comprise sea mustard, laminaria, seaweed fusiforme, gulfweed, *Ecklonia stolonifera*, rhubarb, and *Potamogeton oxyphyllus*. In some embodiments, the green algae comprise green laver, sea lattuce, *Monostroma nitidum*, and sea staghorn.

In some embodiments, the hydrolysate is derived from an extract of a seaweed selected from the group consisting of red algae, brown algae, green algae and a combination thereof the red algae comprises laver, agar-agar, sea string, and Grateloupiaceae, the brown algae comprises sea mustard, laminaria, seaweed fusiforme, gulfweed, *Ecklonia stolonifera*, rhubarb, and *Potamogeton oxyphyllus*, and the green algae comprises green laver, sea lattuce, *Monostroma nitidum*, and sea staghorn.

In some embodiments, the extract comprises a red algae extract selected from among agar, cellulose, carrageenan, xylan, and mannan, a green algae extract selected from among cellulose, xylan, mannan, starch, fructan, and paramylon, or a brown algae extract selected from among cellulose, alginate, fucoidan and laminaran.

In some embodiments, the hydrolysate is a monosaccharide, a furan compound or an organic acid. In some embodiments, the hydrolysate comprises a compound selected from galactose, glucose, xylose, mannose and a combination thereof when the extract from red algae is hydrolyzed. In some embodiments, the hydrolysate comprises a compound selected from, glucose, xylose, mannose, fructose and a combination thereof when the extract from green algae is hydrolyzed. In some embodiments, the hydrolysate comprises a compound selected from glucose, glucronic acid, fucose, galactose, xylose, mannitol and a combination thereof when the extract from brown algae is hydrolyzed.

In some embodiments, the biofuel comprises an oxygen-containing compound or a biohydrocarbon. In some embodiments, the oxygen-containing compound is selected from ethanol, propanol, butanol, pentanol bexanol and a combination thereof. In some embodiments, the biohydrocarbon is selected from biogasoline, biodiesel, a jet fuel, an additive and a combination thereof.

Still further embodiments provide a method of cleaning, disinfecting or sterilizing an inert surface, comprising contacting the inert surface with an effective amount of a protein having lyase activity comprising an amino acid sequence selected from SEQ ID NO: 2; SEQ ID NO: 3; SEQ ID NO: 4; SEQ ID NO: 5; SEQ ID NO: 6; and SEQ ID NO: 7.

In some embodiments, the inert surface is selected from a prosthetic device; a ventilator, a catheter and an intrauterine device.

Yet other embodiments provide a method of treating, preventing or inhibiting a disease, disorder or condition marked by the presence of biofilm, comprising administering an effective amount of a protein having lyase activity comprising an amino acid sequence selected from SEQ ID NO: 2; SEQ ID NO: 3; SEQ ID NO: 4; SEQ ID NO: 5; SEQ ID NO: 6; and SEQ ID NO: 7, to a body surface of a patient in need thereof.

In some embodiments, the disease, disorder or condition marked by the presence of biofilm is selected from: a urinary tract infection, a catheter-originated infection, a middle-ear infection, dental plaque, gingivitis, an eye infection, endocarditis, cystic fibrosis, and a nosocomial infection.

In some embodiments, the present invention provides a protein comprising an amino acid sequence selected from SEQ ID NO: 2; SEQ ID NO: 3; SEQ ID NO: 4; SEQ ID NO: 5; SEQ ID NO: 6; and SEQ ID NO: 7, wherein the protein is derived from a bacterial genus selected from *Pseudomonas, Achromobacter, Bordetella, Uliginosibacterium* and *Duganella*.

In some embodiments, the present invention provides a protein comprising N167, H168, R215, Y222 residues, wherein the protein is derived from a bacterial genus selected from *Pseudomonas, Achromobacter, Bordetella, Uliginosibacterium* and *Duganella*. In some embodiments, the nucleic acid sequence of SEQ ID NO: 1 is derived from a bacterial genus selected from *Pseudomonas, Achromobacter, Bordetella, Uliginosibacterium* and *Duganella*.

In some embodiments, the present invention provides peptides which have an affinity for a specific target site. For example, skin, oral cavity (soft tissue and hard surfaces, e.g. teeth), a binding protein to a particular extracellular matrix protein or ligand for a cell-surface receptor, and the like. In some embodiments, a peptides which has an affinity for a specific target site is referred to as a "binding peptide". In some embodiments, a binding peptide is fused to any one of the amino acid sequences described herein.

In some embodiments, multiple binding peptides are fused to any one of the amino acid sequences described herein. Multiple binding elements can be linked directly together or they can be linked together using, peptide spaces. Certain peptide spacers/liners are from 1 to 100 or 1 to 50 amino acids in length. In some embodiments, the peptide spaces are about 1 to about 25, 3 to about 40, or 3 to 30 amino acids in length. In other embodiments, the spacers are from about 1 to about 20 or from 5 to about 20 amino acids in length.

In some embodiments, the amino acid sequences described herein, themselves contain domains which have an affinity for particular body surfaces.

The invention will be described in greater detail by way of specific examples. The following examples are offered for illustrative purposes and are not intended to limit the invention in any manner. Those skilled in the art will readily recognize a variety of noncritical parameters, which can be changed or modified to yield essentially the same results.

EXAMPLES

Unless otherwise stated, standard molecular biology techniques were used for subcloning and site-directed mutagenesis. An *Escherichia coli* codon-optimized nucleotide sequence of Smlt1473 was subcloned into pET28a(+) (Invitrogen) as a BamHI-XhoI insert. Mutagenic primers were designed via PrimerX (www.bioinformatics.org/primerX) and point mutations generated via the Quikchange II Site Directed Mutagenesis kit (Agilent Technologies). Nucleotide sequences containing point mutations were confirmed by DNA sequencing (GeneWiz).

Example 1

For expression, constructs are electroporated into *E. coli* BL21 (DE3) cells and plated on LB agar plates containing 50 µg/mL kanamycin. An individual colony is cultured in 5 mL LB medium supplemented with 50 µg/mL kanamycin for 16 hours at 37° C. 200 rpm. Then 2 mL of saturated culture is added to 200 mL LB and incubated for 16 hours at 18° C., 200 rpm. The culture is then diluted to an $OD_{600}$ of 0.8 in 800 mL LB and grown for 1 hour at 18° C., 200 rpm. After 1 hour, protein expression is induced by the addition of 1 mM IPTG and the culture is incubated at 18° C., 200 rpm for another 16-20 hours.

Example 2

For purification, cells are harvested at 8,000 g for 15 minutes at 4° C. washed once in 20 mL of ice-cold PBS, resuspended in 15 mL lysis buffer (100 mM HEPES, 500 mM NaCl, 10% w/v glycerol, 10 mM imidazole) and sonicated at 15 W, 50% duty, 15 minutes total processing time. The soluble cell lysate is clarified by centrifugation at 17,000 g for 20 minutes at 4° C. and hexahistidine tagged Smlt1473 is purified from the sample by immobilized metal ion affinity chromatography (IMAC). Cell lysate is passed over a column containing 15 mL of $Ni^{2+}$-bound Chelating Sepharose Fast Flow resin (GE Healthcare) pre-equilibrated in IMAC Buffer A (20 mM HEPES, 500 mM NaCl, 10% w/v glycerol, 10 mM imidazole) at a flow rate of 1.8 mL/min via a BioLogic LP chromatography system (Bio-Rad) with fraction collector. The column is washed for 70 min with IMAC Buffer A to remove any unbound proteins, before applying a gradient from 0% to 100% IMAC Buffer B (20 mM HEPES, 500 mM NaCl, 10% w/v glycerol, 500 mM imidazole) over the course of 200 minutes. Fractions are assayed for protein content via Bradford reagent (Bio-Rad) and samples containing purified Smlt1473 are pooled together and dialyzed against 4 L of 20 mM sodium phosphate buffer pH 8 for 40 hours at 4° C. with one buffer exchange. Purity is assessed using SDS-PAGE, western blotting and MALDI-TOF. For MALDI-TOF, 1 µL of protein sample is mixed with 1 µL of sinapinic acid matrix, spotted onto a MSP 96 target ground steel plate (Bruker), and allowed to air dry. Samples are then analyzed via a Microflex mass spectrometer (Bruker Daltonics).

Example 3

Two 1 mL samples of cultures induced for 12 hours are harvested by centrifugation at 8,000 g for 10 minutes at 4° C. One pellet is resuspended in 200 µL of 4 M urea and designated the whole cell lysate sample. The second pellet is resuspended in 200 µL of ice-cold sucrose buffer (20 mM HEPES, 1 mM EDTA, 20% w/v sucrose), incubated on ice for 15 minutes, centrifuged, resuspended in 200 µL ice-cold 5 mM $MgSO_4$, and incubated on ice for 15 minutes. The resulting supernatant containing the periplasmic proteins is collected by centrifugation at 17,000×g for 10 minutes at 4° C.

Example 4

Forty (40) µL of protein sample mixed with 10 µL of 5× Lammeli sample buffer is heated for 5 minutes at 90° C. before loading 10 µL onto a 4% stacking/12% separating acrylamide gel with MES running buffer. Five (5) µL of Precision Plus Protein All Blue Standard (Bio-Rad) is used as a molecular weight standard. Samples are run at 100 V and transferred to a nitrocellulose membrane (Amersham Hybond ECL) for 90 minutes at 17 V. 4° C. Transfer is confirmed by staining the membrane with 0.1% Ponceau S stain. The membrane is then blocked overnight at 4° C. with 5% fat-free milk in TBST, washed once with TBST, incubated for 1 hour at room temperature with mouse monoclonal anti-hexahistidine tag primary antibody (Cell Signaling) diluted 3000 fold in 5% fat-free milk, washed five times with TBST, incubated for 1 hour at room temperature with horseradish peroxidase-conjugated anti-mouse IgG secondary antibody (Cell Signaling) diluted 3000 fold in 5% fat-free milk, washed five times with TBST, and then twice with TBS. The membrane is developed with a chemiluminescent horseradish peroxidase substrate (GE Healthcare) and imaged with a Storm 860 scanner.

Example 5

Five (5) μL of induced culture is spotted onto LB plates solidified with 1% agarose and supplemented with 50 μg/mL kanamycin and 1 mg/mL of polyManA or polyGlcA. Plates are incubated at room temperature for 12 hours, gently flooded with 10% cetyl pyridinium chloride, and incubated at room temperature for 30 minutes. A clearing zone surrounding the area treated with culture is indicative of extracellular lyase activity.

Example 6

Sodium alginate, medium viscosity, is obtained from MP Biomedicals. Hyaluronic acid potassium salt from human umbilical cord is obtained from The Wistar Institute. PolyGlcA is prepared from Avicel PH105 (FMC Biopolymer) by first converting the microcrystalline cellulose to regenerated amorphous cellulose by dissolution in 86.2% $H_3PO_4$ and then converting the regenerated amorphous cellulose to polyGlcA via 2,2,6,6-tetramethylpipelidine-1-oxyl radical (TEMPO)-NaBr-NaClO mediated oxidation. PolyGlcA samples are precipitated with ethanol, dried, resuspended in $ddH_2O$ and dialyzed against 4 L of $ddH_2O$ for 40 hours at 4° C. with one buffer exchange, polyManA, polyGulA, and polyMG block structures are prepared from sodium alginate by partial acid hydrolysis as described by previously. Each fraction is resuspended in $ddH_2O$ and dialyzed against 4 L of $ddH_2O$ for 40 hours at 4° C. with one buffer exchange. Sugar concentration is determined via the phenol-sulfuric acid method. The composition of each alginate fraction is determined via circular dichroism. Briefly, 300 μL of a 5 mg/mL solution of each fraction is added to a 1 mm pathlength quartz cuvette (Starna) and ellipticity measured from 190 to 260 nm in a J-815 circular dichroism spectrometer (JASCO). The scan speed is 200 nm/min; with three accumulations per sample. The polyManA fraction is calculated to contain 85.4±0.6% ManA, the polyMG fraction 54.1±0.4% ManA, and the polyGulA fraction 17.3±1.6% ManA. Circular dichroism spectra and associated calculations are used to determine polysaccharide composition.

Example 7

The β-elimination mechanism of PLs results in the formation of a double bond whose accumulation is monitored by measuring the change in absorbance at 235 nm. Absorbance measurements are made in 1 second intervals using an Ultrospec 3300 pro UV-Vis spectrophotometer with a detection limit of 0.001 absorbance units at 235 nm per minute. One unit (U) of enzyme activity is defined as an increase in absorbance at 235 nm of 1.0 per minute at 25° C. (1 U=1 $\Delta A_{235nm}$ $min^{-1}$) (28-30). 17.5 μg of purified Smlt1473 is added to a final volume of 350 μL for reactions containing alginate, polyManA, polyGulA, polyMG, or HA. Due to the higher activity against polyGlcA versus all other substrates, 1.75 μg of protein is added to reactions containing polyGlcA. The pH of all reactions is maintained by using a specific buffer for a given pH (Acetate for pH 4-6, Phosphate for pH 6-8, Tris for pH 6.5-9, Glycine for pH 9-10) at a total ionic strength of 30 mM. For the determination of optimal pH and buffer conditions, the enzyme is incubated in a given buffer without substrate for 10 minutes before being added to a solution containing a final polysaccharide concentration of 1 mg/mL in the same buffer. For the determination of Michaelis constant ($K_M$) and maximum velocity ($V_{MAX}$) for each substrate, polysaccharide concentration (S) is varied from 0.0625 mg/mL to 2 mg/mL and initial rates ($\upsilon_i$) are fitted to the Michaelis-Menten equation, $\upsilon = V_{MAX}S/(K_M+S)$, with generalized reduced gradient (GRG2) nonlinear optimization program. For all substrates, R-squared and correlation values are greater than 0.965 and 0.985, respectively. Lyase activity is also confirmed by measuring the concentration of the resulting deoxy sugar via the thiobarbituric acid (TBA) method as described previously.

Example 8

HPLC experiments are run on an Agilent 1100 series HPLC value system equipped with a 96-well autosampler and UV-Vis detector. Smlt1473 at a final concentration of 50 μg/mL (5 μg/mL for polyGlcA samples) is added to either polyManA (3 mg/mL, 30 mM Tris pH 9), polyGlcA (3 mg/mL, 30 mM Tris pH 7), or HA (1 mg/mL, 30 mM Acetate pH 5) at final concentrations and buffers indicated in parenthesis. 15 μL of the reaction mixture is injected at 30-minute intervals over the course of 24 hours onto a TSKgel SuperOligoPW column (Tosoh) equipped with corresponding guard column. The mobile phase is 20 mM sodium phosphate buffer pH 8 plus 250 mM NaCl and the flow rate is 0.275 mL/min. Unsaturated uronic acid products are detected by absorbance at 235 nm. A series of PEG standards are used to generate a calibration curve.

Example 9

Recombinant Smlt1473 is purified to homogeneity from E. coli lysates via IMAC and purity is confirmed by immunoblotting and MALDI-TOF. The enzymatic activity of purified Smlt1473 (SEQ ID NO: 2) is tested against the following polyuronides: alginate, polyManA, polyGulA, polyMG, polyGlcA, and hyaluronic acid. The results of this evaluation are illustrated in Table 2 (below), in which initial rates for each substrate (1 mg/mL) are given at their respective optimal pH values.

TABLE 2

| Substrate | pH | Specific Activity (U/mg) |
| --- | --- | --- |
| Alginate | 9 | 20.4 ± 0.7 |
| Polymannuronic Acid (polyManA) | 9 | 68.5 ± 2.9 |
| PolyGulA | 9 | 2.1 ± 0.2 |
| polyMG | 9 | 12.8 ± 0.4 |
| Polyglucuronic Acid (polyGlcA) | 7 | 848.3 ± 6.3 |
| Hyaluronic Acid (HA) | 5 | 42.3 ± 1.3 |

Of particular note, specific activities for each of the three most active substrates (polyManA, polyGlcA, HA) are found to be strongly dependent on pH, with optimal activity for HA at pH 5, polyGlcA at pH 7 and polyManA at pH 9 (FIG. 1). The highest overall specific activity (848.3±6.3 U/mg at pH 7) was for polyGlcA (FIG. 1A), which is among the highest reported for polyGlcA-specific lyases. For poly- ManA the specific activity (68.5±2.9 U/mg at pH 9) was also significant (FIG. 1B), being within an order of magnitude to reported values for polyManA-specific lyases. Likewise, while the specific activity for HA (42.3±1.3 U/mg at pH 5) was the lowest for the three major substrates (FIG. 1C), it is within an order of magnitude of reported values for bacterial hyaluronidases. Optimal pH values for each substrate were independently confirmed by the TBA method (FIG. 1D). Kinetic parameters for each of the three substrates were also determined according to the Michaelis-Menten equation described in Table 3 (below), with $V_{MAX}$ values similar in magnitude and trend to the specific activities for each of the three main substrates (polyManA, polyGlcA, HA); $V_{MAX}$ for polyGlcA is approximately 10-fold greater versus polyManA or HA.

TABLE 3

| Substrate | Buffer | $K_M$ (mg mL$^{-1}$) | $V_{MAX}$ ($\Delta A_{235\ nm}$ min$^{-1}$ mg$^{-1}$) |
|---|---|---|---|
| polyGlcA | 30 mM Tris pH 7 | 0.14 | 940.04 |
| polyManA | 30 mM Tris pH 9 | 0.26 | 91.57 |
| HA | 30 mM Acetate pH 5 | 0.55 | 71.50 |

The $K_M$ values for the three substrates also follow a similar trend to $V_{MAX}$ and specific activity, with a 5-fold larger $K_M$ for HA versus polyGlcA. Thus, based on the highest specific activity for polyGlcA (FIG. 1A), one could tentatively conclude that Smlt1473 is a polyGlcA-specific lyase. However, the multiple pH optima exhibited by Smlt1473 for maximal HA, polyGlcA and polyManA cleavage (FIG. 1), as well as comparable kinetic parameters and specific activities to published values for lyases specific to each of these substrates, indicate that Smlt1473 is a multifunctional PL with potent activity against polyManA, polyGlcA and HA.

Example 10

As stated previously, the β-elimination mechanism of PLs requires a neutralizing group, proton acceptor, and protein donor. Despite diverse substrate specificity, secondary structure content, and tertiary folds, the residues responsible for each of the aforementioned roles appears to be highly conserved across many polysaccharide lyase families. Based on sequence alignments with related polysaccharide lyases using COBALT, four conserved, active-site residues in Smlt1473 were identified (N167, H168, R215, and Y222) and predicted inactivating mutants (N167L, H168A, R215L, and Y222F) were expressed, purified and characterized. Enzymatic activity of each mutant was observed directly from a plate assay with polyGlcA and polyManA as the substrates, and quantified in terms of the change in absorbance at 235 nm and TBA method. All four mutations (N167L, H168A, R215L, and Y222F) were found to abolish activity against all three substrates (polyGlcA, polyManA, HA) with the exception of H168A, which retained low activity (10% of wild-type) against polyGlcA at pH 7. Interestingly, while the H168A mutant retained approximately 10% of wild-type activity against polyGlcA, its specific activity (59.9±1.8 U/mg at pH 7) was comparable to optimal, wild-type Smlt1473 activity against polyManA (68.5±2.9 U/mg at pH 9) and HA (42.3±1.3 U/mg at pH 5). To confirm that the mutant lyases retained secondary structure equivalent to wild-type, CD spectra were collected for wild-type and each mutant (N167L, H168A, R215L, and Y222F). For wild-type and mutant Smlt1473, a predominantly α-helical secondary structure was observed in terms of specific minima at 208 nm and 222 nm. The calculated percent helicity for wild-type was 48.3%, with less than 5% change in percent helicity for each mutant, indicating the overall secondary structure was not perturbed significantly by the mutations. Therefore, the catalytic mechanism of Smlt1473 is dependent on four highly conserved residues (N167, H168, R215, Y222) that are consistent with an Asn/Arg-Tyr/His neutralization-acid/base mechanism.

Example 11

Various concentrations of alginic acid are added to 0.1 mg/mL samples of SEQ ID NO: 2. Reaction velocities are calculated from the absorbance at 235 nm generated from unsaturated products of alginic acid. The data described in Table 4 (below) demonstrates that the reaction velocity increases With increases in alginic acid concentration.

TABLE 4

| Time (min) | 0.25 mg/mL | 0.5 mg/mL | 1 mg/mL | 1.5 mg/mL |
|---|---|---|---|---|
| | | Absorbance (235 nm) | | |
| 0 | 0 | 0 | 0 | 0 |
| 20 | 0.66 | 1.02 | 1.59 | 2.05 |
| 40 | 0.93 | 1.27 | 1.95 | 2.32 |
| 60 | 1.10 | 1.58 | 2.09 | 2.28 |
| 80 | 1.13 | 1.84 | 2.14 | 2.26 |
| 100 | 1.14 | 1.97 | 2.16 | 2.24 |

Example 12

Thermal stability of an exemplary protein of the present invention is evaluated by adding a sample of alginic acid to a fixed concentration of an exemplary protein of the present invention. The mixture is then heated to a temperature of about 50 deg. C. for approximately 10 minutes, and then cooled rapidly to room temperature (20 deg. C.). Initial reaction velocities are calculated from the absorbance at 235 nm generated from unsaturated products of alginic acid. The data described in Table 5 (below) demonstrates the thermal stability of an exemplary protein of the present invention, as it is able to maintain activity at temperatures in excess of 50 deg. C.

TABLE 5

| Temperature | Initial Velocity ($A_{235}$/min/mg protein) |
|---|---|
| 20° C. | 2.40 |
| 50° C. to 20° C. | 2.46 |

Example 13

Reaction velocities of wild-type and mutant enzymes of the present invention are evaluated. 1 mg/mL samples of alginic acid are added to a 0.1 samples of wild-type (WT) and mutant enzymes (Y115F, W171A, H221F and Y225F). Reaction velocities are calculated from the absorbance at 235 nm generated from unsaturated products of alginic acid. The data provided in Table 6 (below) describes the results of this evaluation.

TABLE 6

| Time (min) | Protein | | | | |
|---|---|---|---|---|---|
| | WT | Y115F | W171A | H221F | Y225F |
| | Reaction Velocity (A$_{235}$/mg protein) | | | | |
| 0 | 0 | 0 | 0 | 0 | 0 |
| 10 | 0.647 | 0.521 | 1.187 | 0.780 | 0.885 |
| 20 | 2.053 | 1.623 | 7.202 | 3.067 | 3.456 |
| 30 | 2.335 | 1.840 | 10.022 | 3.664 | 4.127 |
| 40 | 2.447 | 1.925 | 11.527 | 3.918 | 4.404 |
| 50 | 2.507 | 1.971 | 12.463 | 4.059 | 4.561 |
| 60 | 2.545 | 1.999 | 13.101 | 4.148 | 4.660 |

Example 14

The degradation of celluronic acid by a fixed concentration of an exemplary protein of the present invention (SEQ ID NO: 2) in the presence of various detergents (1%) and acids is evaluated. The data described in Table 7 (below) demonstrates that stability (insensitivity) of an exemplary protein of the present invention to various detergents. Activity is measured in terms of the percentage of activity of the SEQ ID NO: 2 in the absence of a detergent.

TABLE 7

| Detergent | Percent Activity |
|---|---|
| Octyl glucoside | 94.5 |
| Lauryldimethylamine N-oxide (LDAO) | 110.9 |
| n-Decyl-β-D-thiomaltoside (Anapoe C10 E6) | 79.4 |
| Tween-20 | 101.4 |

Example 15

Initial reaction velocities are measured for exemplary proteins of the present invention (SEQ ID NO: 2 [WT], Y115F, W171A, H221F and Y225F). Samples of celluronic acid are added to samples of exemplary proteins of the present invention. The data provided in Table 8 (below) describes the results of this evaluation.

TABLE 8

| Protein | Initial Velocity (A$_{235}$/min/mg protein) |
|---|---|
| WT | 2.47 |
| Y115F | 2.29 |
| N167L | 0.17 |
| W171A | 9.45 |
| H221F | 4.77 |
| Y225F | 6.71 |

It is intended that any patents, patent applications or printed publications, including books, mentioned in this patent document be hereby incorporated by reference in their entirety.

As those skilled in the art will appreciate, numerous changes and modifications may be made to the embodiments described herein, without departing from the Spirit of the invention. It is intended that all such variations fall within the scope of the invention.

The invention claimed is:

1. An isolated recombinant protein, having the amino acid sequence of SEQ ID NO: 2.

2. A composition comprising an isolated recombinant protein according to claim 1; and a carrier.

3. A method of cleaning, disinfecting, or sterilizing an inert surface, comprising contacting said surface with an effective amount of an isolated recombinant protein according to claim 1.

4. The method of claim 3, wherein the inert surface is selected from a prosthetic device; a ventilator, a catheter and an intrauterine device.

5. A method of treating or inhibiting a disease, disorder or condition marked by the presence of biofilm on a body surface, comprising administering an effective amount of an isolated recombinant protein according to claim 1, to a body surface of a patient in need thereof.

6. The method of claim 5, wherein the disease, disorder or condition marked by the presence of biofilm on a body surface is selected from: a urinary tract infection, a catheter-originated infection, a middle-ear infection, dental plaque, gingivitis, an eye infection, endocarditis, cystic fibrosis, and nosocomial infections.

7. A method of treating or inhibiting a disease, disorder or condition marked by an abnormal level of hyaluronic acid comprising administering an effective amount of an isolated recombinant protein according to claim 1, to a body surface of a patient in need thereof.

8. The method of claim 7, wherein the disease; disorder or condition marked by an abnormal level of hyaluronic acid is a disease, disorder or condition of the epithelial, connective or neural tissue.

9. The method of claim 8, wherein the disease, disorder or condition marked by an abnormal level of hyaluronic acid is cancer.

10. The method of claim 9, wherein the administration of an effective amount of an isolated recombinant protein according to claim 1, inhibits tumor progression.

11. A method of improving delivery of an intravenous composition, comprising contacting an injection site of a subject with an effective amount of an isolated recombinant protein according to claim 1, and administering an intravenous composition to said subject via said injection site.

12. The method according to claim 11, wherein the subject is below the age of 18.

13. The method according to claim 12, wherein the subject is below the age of 12.

* * * * *